United States Patent [19]
Jarvis et al.

[11] 4,247,526
[45] Jan. 27, 1981

[54] METHOD FOR PREPARING DICALCIUM PHOSPHATE DIHYDRATE WITH IMPROVED STABILITY

[75] Inventors: William M. Jarvis, Webster Groves; Keun Y. Kim, Clayton, both of Mo.

[73] Assignee: Monsanto Company, St. Louis, Mo.

[21] Appl. No.: 43,412

[22] Filed: May 29, 1979

[51] Int. Cl.³ .................... C01B 00/00; C01B 15/16; C01B 25/26

[52] U.S. Cl. .................................. 423/266; 423/267; 423/308; 423/311; 424/57

[58] Field of Search .............. 423/265, 266, 267, 307, 423/308, 309, 311, 313; 424/57

[56] References Cited

U.S. PATENT DOCUMENTS

| | | | |
|---|---|---|---|
| 2,852,341 | 9/1958 | Bell et al. | 423/308 |
| 3,012,852 | 12/1961 | Nelson | 423/267 |
| 3,066,056 | 11/1962 | Schlaeger et al. | 423/267 |
| 3,464,786 | 9/1969 | Harnisch et al. | 423/313 |

*Primary Examiner*—O. R. Vertiz
*Assistant Examiner*—Gregory A. Heller
*Attorney, Agent, or Firm*—S. M. Tarter; W. H. Duffey; F. D. Shearin

[57] ABSTRACT

Dicalcium phosphate dihydrate containing a sufficient amount of trimagnesium phosphate and/or tetrasodium pyrophosphate to inhibit spontaneous hydrolysis and/or decomposition of the dicalcium phosphate dihydrate is widely used as a dental polishing agent with and without added fluoride. Now it has been found that dicalcium phosphate dihydrate containing a sufficient amount of pyrophosphate to provide hydrolytic stability to the dicalcium phosphate can have improved fluoride stability when about 0.1 weight percent to about 5 weight percent of trimagnesium phosphate, and about 0.1 weight percent to about 3 weight percent of at least one pharmaceutically acceptable condensed phosphate salt is added to the formulation. In the preferred embodiment less than 2 percent sodium tripolyphosphate provides satisfactory results.

10 Claims, No Drawings

METHOD FOR PREPARING DICALCIUM PHOSPHATE DIHYDRATE WITH IMPROVED STABILITY

BACKGROUND OF THE INVENTION

The present invention relates to a method of preparing dentifrice abrasives, and more particularly to dicalcium phosphate dihydrate with improved stability.

Dicalcium orthophosphate dihydrate ($CaHPO_4 \cdot 2H_2O$) that has been stabilized against spontaneous hydrolysis and/or decomposition with a small amount of tetrasodium pyrophosphate in accordance with the processes such as those described by Moss et al in U.S. Pat. No. 2,287,699 or with trimagnesium orthophosphate and the like has been utilized in dental preparations for many years. Indeed, dicalcium phosphate dihydrate frequently is stabilized against spontaneous hydrolysis and/or decomposition with a small amount of both tetrasodium pyrophosphate and trimagnesium phosphate in dental preparations.

Furthermore, as is known to those skilled in the art, dentifrice formulations using dicalcium phosphate dihydrate frequently contain sodium or potassium monofluorophosphate as a source of fluoride ion to inhibit or retard the formation of dental caries. Thus, the use of dicalcium phosphate dihydrate with sodium or potassium monofluorophosphate and stabilized against spontaneous hydrolysis and/or decomposition with tetrasodium pyrophosphate and/or trimagnesium phosphate, either with or without other polishing agents, are well known to those skilled in the art.

Although satisfactory results are obtained using the dental formulations as set forth above, it has been found that over a period of time the soluble fluoride is lost from the dental formulations. For example, it has been found that dental formulations containing dicalcium phosphate dihydrate stabilized with tetrasodium pyrophosphate at up to 1 weight percent by weight $P_2O_5$, as pyrophosphate, or about 2 weight percent trimagnesium phosphate octahydrate, and sufficient sodium monofluorophosphate to provide about 1,000 parts per million soluble fluoride will lose a substantial amount of the soluble fluoride after prolonged storage. Only a small improvement is seen when both trimagnesium phosphate and tetrasodium pyrophosphate are used together with respect to soluble fluoride stability.

Although Applicants do not wish to be bound by any particular theory, it is believed that the loss of soluble fluoride in the formulation is related to the hydrolytic instability of the dicalcium phosphate dihydrate. It is believed that fluoride ion catalyzes the formation of calcium hydroxyapatite which then reacts with the soluble fluoride to form water-insoluble calcium fluoroapatite and/or calcium fluoride. Hence, it can be seen that improved fluoride stability of dicalcium phosphate dihydrate may improve stability against spontaneous hydrolysis and/or decomposition.

In any event, it can be seen that there is a need for a method of preparing dicalcium phosphate dihydrate which will provide greater amounts of soluble fluoride after prolonged storage. Now, a method to meet this need is provided.

SUMMARY OF THE INVENTION

These and other needs are achieved by a method which comprises:

(A) providing dicalcium phosphate dihydrate containing a sufficient amount of pyrophosphate complex to provide at least some hydrolytic stability to the DCPD;

(B) adding to the dicalcium phosphate dihydrate from about 0.1 weight percent to about 5 weight percent trimagnesium phosphate, based on the weight of the dicalcium phosphate dihydrate; and (C) adding to the dicalcium phosphate dihydrate from about 0.1 weight percent to about 3 weight percent of a pharmaceutically acceptable condensed phosphate salt, based on the weight of the dicalcium phosphate dihydrate.

The term "DCPD" as it is used in the specification and claims shall mean dicalcium phosphate dihydrate. The term "pyrophosphate complex" shall mean the chemical composition that is formed when a salt of a soluble pyrophosphate or calcium-alkali metal pyrophosphate is added to DCPD during the precipitation stage to provide conventional hydrolytic stability to the DCPD. The term "hydrolytic stability" with respect to DCPD shall mean DCPD that has been stabilized against spontaneous hydrolysis and/or decomposition.

DCPD containing the pyrophosphate complex can be prepared by any number of techniques known to those skilled in the art. Generally, a basic calcium-containing material such as calcium carbonate, calcium oxide, calcium hydroxide and mixtures thereof, including mixtures commonly known as slaked lime, quick lime and hydrated lime, are added to dilute aqueous solutions of orthophosphoric acid to precipitate DCPD. Then, hydrolytic stability of the DCPD from the pyrophosphate complex is achieved by adding a calcium/sodium pyrophosphate or a soluble pyrophosphate salt to the DCPD such as is disclosed in U.S. Pat. Nos. 2,287,699; 3,012,852; 3,169,096; 3,411,873 and the like.

In the preferred embodiment, the DCPD is prepared by adding 0.3 weight percent $P_2O_5$ equivalent of tetraalkali metal pyrophosphate to an aqueous mixture containing DCPD having a pH from about 5.5 to about 6.5 and then adding a sufficient amount of lime to the DCPD slurry to provide a pH from about 6.5 to about 8.0.

The soluble pyrophosphate salts useful for preparing the pyrophosphate complex are well known to those skilled in the art. Tetraalkali metal pyrophosphates such as tetrasodium pyrophosphate and tetrapotassium pyrophosphate are preferred, and tetrasodium pyrophosphate is especially preferred to form the pyrophosphate complex. The amount of soluble pyrophosphate salt to be added to the DCPD to provide partial hydrolytic stability ranges from about 0.1 to about 5 percent by weight of $P_2O_5$, as pyrophosphate, based on the weight of the DCPD. It is preferred to add the soluble pyrophosphate salt in an amount corresponding to an addition of from about 0.5 to about 2.5 percent by weight of $P_2O_5$, as pyrophosphate, based on the weight of the DCPD. On yet another basis, the soluble pyrophosphate salt is added in an amount which results in a DCPD containing from about 0.2 to about 2.5 percent by weight of pyrophosphate $P_2O_5$, which would represent typical stabilized DCPD.

After the DCPD containing the pyrophosphate complex is recovered from the slurry and dried, trimagnesium phosphate is added by techniques known to the art, as for example, blending powdered trimagnesium phosphate with the DCPD. The amount of trimagnesium phosphate that can be used in the composition of the present invention can vary within wide limits. The beneficial effects of the trimagnesium phosphate are generally not observed at concentrations less than about 0.1 weight percent, based on the weight of the DCPD, and additional stability is not seen at concentrations above about 5 weight percent, based on the weight of the DCPD. It is preferred to add between about 0.5 weight percent and about 3 weight percent, based on the weight of the DCPD.

In addition, the trimagnesium phosphate used in the method of the present invention is generally added as the octahydrate. However, other hydrates of magnesium phosphate may be equivalent since the exact form of the effective magnesium phosphate after it has been incorporated into a DCPD-based toothpaste formulation is not known. Hence, anhydrous trimagnesium phosphate or trimagnesium phosphates containing 8 to 22 waters of hydration, or even dimagnesium phosphate hydrates, are deemed to be equivalent for purposes of this invention, although the use of trimagnesium phosphate with 8 waters of hydration is preferred.

According to the process of the present invention there is also added to the DCPD from about 0.1 weight percent to about 3 weight percent, based on the weight of the DCPD, of at least one pharmaceutically acceptable condensed phosphate salt. The pharmaceutically acceptable condensed phosphate salt can be added to the DCPD by techniques known to the art, such as by blending the powdered condensed phosphate salt with the DCPD.

In the method of the present invention, the pharmaceutically acceptable condensed phosphate salt and the trimagnesium phosphate can be added to the DCPD containing the pyrophosphate complex at any stage before the DCPD is incorporated into a toothpaste formulation. The order of addition is not believed to be important, but we prefer to add the trimagnesium phosphate to the DCPD before we add the pharmaceutically acceptable condensed phosphate salt.

Any number of pharmaceutically acceptable condensed phosphate salts known to those skilled in the art can be used in the method of the present invention. Sodium, ammonium and potassium salts, either singly or admixed together or with other elements such as calcium and the like, are generally considered to be pharmaceutically acceptable. Hence, suitable condensed phosphate salts include the pharmaceutically acceptable salts of: pyrophosphates, such as tetrasodium pyrophosphate, tetrapotassium pyrophosphate, disodium dihydrogen pyrophosphate (commonly called sodium acid pyrophosphate), anhydrous or the hexahydrate, trisodium or tripotassium pyrophosphate, and the like; polyphosphates such as pentasodium tripolyphosphate, pentapotassium tripolyphosphate and hydrogen containing sodium or potassium tripolyphosphates ($Na_4HP_3O_{10}$, $K_3H_2P_3O_{10}$) and the like; ultraphosphates; metaphosphates, such as sodium metaphosphate and potassium metaphosphate and the like. Pentasodium tripolyphosphate is preferred.

In addition to the above condensed phosphate salts, amorphous condensed phosphates can be used in the present method, such as the sodium phosphate glasses which extend from pure $P_2O_5$ to a composition near a $Na_2O/P_2O_5$ mole ratio of 1.7. The glass with the mole ratio of 1.0 is called hexametaphosphate (sometimes Graham's salt) and other glasses have been called polyphosphates with the degree of polymerization given by proximate analysis.

Pharmaceutically acceptable salts of a compound having only one phosphorous atom, such as an orthophosphate, does not provide as much stability to the DCPD as provided by condensed phosphates, although their presence in the DCPD prepared by the method of the present invention is not harmful. Indeed, it may be desirable to add such a compound along with the condensed phosphate to obtain maximum fluoride stability.

The amount of the pharmaceutically acceptable condensed phosphate salt can vary within wide limits. Although beneficial effects are observed at concentrations as low as about 0.1 percent, based on the weight of the DCPD, it is preferred to use higher concentrations, say greater than about 0.3 weight percent. There does not seem to be a beneficial effect in using more than about 3 weight percent, based on the weight of the DCPD, and the presence of higher concentrations of condensed phosphates may degrade soluble fluoride stability to some degree. The exact concentration of the pharmaceutically acceptable condensed phosphate salts will depend upon a number of factors, as will occur to those skilled in the art in view of the present disclosure, such as the amount of trimagnesium phosphate and the amount of the pyrophosphate complex, the grade of the DCPD, the particular condensed phosphate salt used and the like. However, it is preferred to add between about 0.3 weight percent and about 2 weight percent, based on the weight of the DCPD.

The mechanism by which the pyrophosphate complex and the trimagnesium phosphate and the condensed phosphate salts provide the superior soluble fluoride stability to DCPD is not understood. At first, it was believed that since the condensed phosphate salts are known to be strong calcium sequestering agents, the superior results were achieved by this action. However, when a DCPD composition containing the pyrophosphate complex and trimagnesium complex was admixed with trisodium nitrilotriacetate or tetrasodium ethylenediamine tetraacetate, the hydrolytic stability of the resulting DCPD was not as good as the stability obtained by the present method.

The DCPD prepared by the present method can be used in toothpaste formulations with alkali metal monofluorophosphates such as sodium monofluorophosphate, potassium monofluorophosphate and the like. Sodium monofluorophosphate is preferred for use with DCPD.

The DCPD prepared by the present method can be combined with other dental polishing agents, as will occur to those skilled in the art. Such dental polishing agents include, but are not limited to, insoluble metaphosphates, silica gels, alumina, chalk and the like. Although satisfactory results are achieved using the DCPD prepared by the present method, it may be desirable to add an additional polishing agent such as anhydrous dicalcium orthophosphate, i.e., precipitated anhydrous dicalcium orthophosphate, in order to clean teeth that are very heavily coated with discoloring material, food particles, tartar and the like. The preparation of such DCPD containing a minor amount of such additional polishing agents is known to those skilled in the art, such as described in U.S. Pat. No. 3,334,979.

In the formation of finished dentifrice compositions containing DCPD prepared by the present method, practically any of the auxiliary agents that are conventionally utilized in toothpastes and/or tooth powder formulations can be used. Toothpastes, for example, will generally contain: a source of fluoride ion, such as sodium monofluorophosphate; a sweetener, such as saccharin; a humectant, such as sorbitol or glycerine; a binding agent, such as hydroethyl cellulose, carboxymethyl cellulose, and the like; a sudsing agent, such as sodium lauryl sulfate, sucrose monolaurate or tridecyl alcohol that has been reacted with from about 3 to about 10 moles of ethylene oxide per mole of alcohol; and a flavoring agent.

In toothpastes, the level of the DCPD that is utilized can generally be varied from about 20 to about 60 weight percent, and preferably from about 30 to about 45 weight percent of the formulation. As noted above, the DCPD prepared by the present method need not be the only polishing agent in the dentifrice formulation, although it is generally preferred that DCPD represents at least about half of all of the polishing agents in the dentifrice formulation.

DESCRIPTION OF THE PREFERRED EMBODIMENTS

This invention is illustrated by, but not limited to, the following Examples wherein all percentages are by weight unless otherwise indicated.

EXAMPLE I

An aqueous slurry containing DCPD is prepared by the reaction of phosphoric acid and lime in an aqueous media. The resulting slurry contains approximately 30 percent DCPD and the slurry pH is 5.8.

A 2780 gram sample of the DCPD aqueous slurry with pH adjusted to 6.5 using lime slurry (13.5 percent CaO) is charged to a one gallon reactor equipped with stirrer. There is added to this slurry 188 grams of a 9 percent TSPP aqueous solution (2 percent TSPP based on the DCPD present) and the mixture is stirred for 45 minutes at about 29° C. The pH is then adjusted to about 7.7 with aqueous lime slurry (13.5 percent CaO) and the solid DCPD product is separated from the slurry, dried and milled. A small portion of the sample was separated and the $P_2O_5$ levels corresponding to the pyrophosphate complex present is determined substantially in accordance with the well known ion exchange method for analysis of sodium triphosphate [ASTM D-2671-70 (reapproved 1975), entitled "Standard Method for Analysis of Sodium Triphosphate by the Simplified Ion Exchange Method]. The pyrophosphate complex content is found to be about 0.5 percent.

Portions of the above DCPD containing the pyrophosphate complex, after drying and milling, are blended with powdered trimagnesium phosphate and/or powdered condensed phosphates, and used to prepare a toothpaste formulation similar to that disclosed in U.S. Pat. No. 3,308,029 issued Mar. 7, 1967 which is typical of those that are commercially available, except for flavor. It contains about 1,000 ppm added fluoride. The formulation is set forth below:

|  | Parts by Weight |
|---|---|
| Glycerine | 21.8 |
| DCPD | 49.6 |
| Sodium Lauryl Sulfate | 1.5 |
| Saccharin | 0.2 |
| Water | 25.2 |
| Sodium Monofluorophosphate | 0.8 |
| Carboxymethyl Cellulose | 0.9 |
|  | 100.0 |

Samples of the above paste are transferred to plastic bottles. Thereafter, the plastic bottles are stoppered and placed in an oven at 50° C. for six weeks as an accelerated test to simulate two years storage at ambient temperature. After the six weeks storage, the bottles are removed from the oven and the soluble fluoride concentration of the formulation is measured potentiometrically. The results of the storage after six weeks are shown in Table 1.

TABLE 1

FLUORIDE STABILITY

| | POWDERED ADDITIVE TO DCPD[a] | | SOLUBLE F REMAINING |
|---|---|---|---|
| RUN | Identity | Wt % | (ppm) |
| 1 | — | — | 190 |
| 2 | Sodium Tripolyphosphate | 1 | 290 |
| 3 | Trimagnesium Phosphate | 2 | 390 |
| 4 | Trimagnesium Phosphate | 3 | 390 |
| 5 | Trimagnesium Phosphate | 2 | 430 |
|   | Glassy Sodium Polyphosphate[b] | 1 | |
| 6 | Trimagnesium Phosphate | 2 | 455 |
|   | Sodium Hexametaphosphate | 1 | |
| 7 | Trimagnesium Phosphate | 2 | 490 |
|   | Sodium Trimetaphosphate | 1 | |
| 8 | Trimagnesium Phosphate | 2 | 490 |
|   | SQ Glassy Phosphate[c] | 1 | |
| 9 | Trimagnesium Phosphate | 2 | 495 |
|   | Tetrasodium Pyrophosphate | 1 | |
| 10 | Trimagnesium Phosphate | 2 | 565 |
|   | Pentasodium Tripolyphosphate | 1 | |

[a]DCPD containing 0.5 percent pyrophosphate complex
[b]containing about 200 phosphorus atoms
[c]available commercially from Monsanto Company, St. Louis, Missouri

EXAMPLE II

The procedure of Example I is repeated. The added soluble fluoride content of the toothpaste formulation is about 1,000 ppm. The results are shown in Table 2.

TABLE 2

FLUORIDE STABILITY

| | POWDERED ADDITIVE TO DCPD | | SOLUBLE F REMAINING |
|---|---|---|---|
| RUN | Identity | Wt % | (ppm) |
| 11 | Trimagnesium Phosphate | 2 | 510 |
| 12 | Trimagnesium Phosphate | 5 | 480 |
| 13 | Pentasodium Tripolyphosphate | 0.5 | 330 |
|    | Sodium Metaphosphate | 0.5 | |
| 14 | Pentasodium Tripolyphosphate | 0.5 | 290 |
|    | Disodium Dihydrogen Pyrophosphate | 0.5 | |
| 15 | Trimagnesium Phosphate | 2 | 570 |
|    | Pentasodium Tripolyphosphate | 2 | |
| 16 | Trimagnesium Phosphate | 2 | 550 |
|    | Pentasodium Tripolyphosphate | 1.5 | |
| 17 | Trimagnesium Phosphate | 2 | 570 |
|    | Pentasodium Tripolyphosphate | 1 | |
| 18 | Trimagnesium Phosphate | 2 | 600 |
|    | Pentasodium Tripolyphosphate | 0.5 | |
|    | Sodium Hexametaphosphate | 0.5 | |
| 19 | Trimagnesium Phosphate | 2 | 590 |
|    | Pentasodium Tripolyphosphate | 0.5 | |
|    | Disodium Dihydrogen Pyrophosphate | 0.5 | |

EXAMPLE III

A sample of the DCPD from Example II is blended with 2 percent trimagnesium phosphate, 1 percent pentasodium tripolyphosphate and 0.05 percent monosodium phosphate. When the DCPD is used in the toothpaste formulation of Example II containing about 1,000 ppm soluble fluoride and stored for six weeks at 50° C., about 610 ppm soluble fluoride remains after the test.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A method which comprises:
   (A) providing dicalcium phosphate dihydrate containing a sufficient amount of pyrophosphate complex to provide at least some hydrolytic stability to the DCPD;
   (B) adding to the dicalcium phosphate dihydrate from about 0.1 weight percent to about 5 weight percent trimagnesium phosphate, based on the weight of the dicalcium phosphate dihydrate; and
   (C) adding to the dicalcium phosphate dihydrate from about 0.1 weight percent to about 3 weight percent of a pharmaceutically acceptable condensed phosphate salt, based on the weight of the dicalcium phosphate dihydrate.

2. A method of claim 1 wherein the amount of pyrophosphate complex is from about 0.1 weight percent to about 5 weight percent $P_2O_5$ equivalent of pyrophosphate complex, based on the weight of the dicalcium phosphate dihydrate.

3. A method of claim 2 wherein the stabilizing amount of pyrophosphate complex is from about 0.5 weight percent to about 2.5 weight percent $P_2O_5$ equivalent of pyrophosphate complex.

4. A method of claim 3 wherein there is added to the dicalcium phosphate dihydrate from about 0.5 weight percent to about 2.5 weight percent trimagnesium phosphate.

5. A method of claim 4 wherein there is added to the dicalcium phosphate dihydrate from about 0.3 weight percent to about 2 weight percent of at least one pharmaceutically acceptable condensed phosphate salt.

6. A method of claim 5 wherein the pharmaceutically acceptable condensed phosphate salt is selected from the group consisting of pentasodium tripolyphosphate, sodium trimetaphosphate, disodium dihydrogen metaphosphate, tetrasodium pyrophosphate, and mixtures thereof.

7. A method of claim 6 wherein the pharmaceutically acceptable condensed phosphate salt is pentasodium tripolyphosphate.

8. A method of claim 6 wherein the pharmaceutically acceptable condensed phosphate salt is a mixture of sodium tripolyphosphate and sodium hexametaphosphate.

9. A method of claim 6 wherein the pharmaceutically acceptable condensed phosphate salt is a mixture of pentasodium tripolyphosphate and disodium dihydrogen pyrophosphate.

10. A method of claim 6 wherein the pharmaceutically acceptable phosphate salt is pentasodium tripolyphosphate mixed with monosodium phosphate.

* * * * *